United States Patent [19]
Shimada

[11] Patent Number: 5,632,768
[45] Date of Patent: May 27, 1997

[54] MOXA TREATMENT DEVICE

[76] Inventor: Osamu Shimada, 996, Shima-machi, Kumamoto City, Kumamoto Pref., Japan

[21] Appl. No.: 384,415

[22] Filed: Feb. 6, 1995

[30] Foreign Application Priority Data

Mar. 30, 1994 [JP] Japan .................. 6-085744

[51] Int. Cl.$^6$ .................................................. A61F 7/00
[52] U.S. Cl. ........................ 607/96; 607/114; 126/204; 126/92 AC; 126/92 B
[58] Field of Search ............... 126/92 AC, 92 B, 126/204, 208, 209; 604/113, 291; 607/96, 114, 108–112

[56] References Cited

U.S. PATENT DOCUMENTS

| | | | |
|---|---|---|---|
| 4,452,225 | 6/1984 | Plant | 126/92 B |
| 4,671,788 | 6/1987 | Wu | 607/96 |
| 4,731,050 | 3/1988 | Harada et al. | 607/96 |
| 4,747,841 | 5/1988 | Kuratomi et al. | 604/291 |
| 5,327,886 | 7/1994 | Chiu | 607/96 |
| 5,417,389 | 5/1995 | Chew et al. | 126/92 B |

*Primary Examiner*—Robert L. Nasser
*Attorney, Agent, or Firm*—Marshall, O'Toole, Gerstein, Murray & Borun

[57] ABSTRACT

This disclosure relates to a moxa treatment device which can be placed stably on the surface of an affected part of a patient, requiring no adjustment of the ignited portion, and can efficiently concentrate the heat from the heat generating block towards the affected part over a long time, thus having a high heat efficiency. The device is provided with a hollow frustum of a cone or pyramid having a top opening and a bottom opening, a heat generating block installed inside the frustum of cone or pyramid, and a cover mounted on said top opening in such a way that the cover can be opened or closed as desired. Said heat generating block is comprised of a porous heat generator supporting block mounted near the top opening of said frustum of cone or pyramid and of a heat generator loaded in the supporting block.

8 Claims, 5 Drawing Sheets

MOXA TREATMENT DEVICE

FIELD AND BACKGROUND OF THE INVENTION

The present invention relates to a moxa treatment device which warms and stimulates the surface of an affected area of a person's body so as to stimulate the body and relieve the pain of the affected area.

Moxa treatment, or moxibustion, has been practiced from ancient times as a folk remedy for relieving the pain of an affected part such as the shoulder, back, waist or knee. Traditionally, a cone of "moxa" in the size of a rice grain is placed on the skin surface of the affected part, then the cone of moxa is lit by a fire of a stick of incense, and its heat of combustion is used to relieve the pain of the affected part. Moxa is made from fibers on the back of dried leaves of mugwort, an herb.

When moxa treatment is given directly on the skin surface of an affected part, the heat of combustion of the cone of moxa may be excessive and cause blisters on the skin surface of the affected part. Accordingly, in recent years, moxa treatment through another substance has been practiced. A thin layer of garlic, leek, miso or the like is placed on the skin surface of an affected part, and moxa is placed and burnt on the top of this layer. Heat is thus transmitted indirectly to the affected surface.

Another method of moxa treatment has also been practiced. Moxa is formed in the shape of a cigarette, one end of the formed moxa is ignited, and this ignited piece is inserted into a cylindrical holder. The holder is held by a hand and placed at the skin surface of an affected part to stimulate the affected part with the heat of combustion of the moxa.

In the case of the former moxa treatment through a layer of another substance, it is not easy to control the combustion of the moxa when placed on the top surface of the substance such as garlic, leak or miso, and the skin may be burnt.

In the case of the moxa treatment device using a cylindrical holder (see, for example, H02-38751/Japan Utility-model Reg. No. 1869300), it requires much trouble to adjust the ignited portion of the moxa in the cylindrical holder and to shift the holder, while it is held in position, to a different point on the affected part. The reason is that the stability of the cylindrical holder is not good. Hence the heat of combustion cannot be concentrated onto the affected part, and the thermal efficiency is low.

SUMMARY OF THE INVENTION

The present invention avoids the above-mentioned problems of the prior art. It is an objective of this invention to provide a moxa treatment device having a high thermal efficiency, wherein a heat generator is ignited and burnt in a container. The container can be stably held on the surface of an affected part, the ignited portion needs no adjustment during the course of the moxa treatment, and the heat of combustion can be efficiently concentrated onto the affected part over a long time.

To accomplish the above-mentioned objectives, the present invention provides a hollow structure having the shape of a cone or pyramid, the structure having an opening in the bottom thereof and with a heat generating block located inside the hollow structure.

The above-mentioned heat generating block may be comprised of a heat generator and a porous heat generator supporting block.

The above-mentioned hollow structure may be comprised of a frustum of a cone or a pyramid having an opening in the top and a cover mounted onto the top opening in such a way that the cover can be opened or closed as desired, and the above-mentioned heat generating block may be located inside the frustum of the structure.

It is desirable to provide a retainer which also serves as a heat reflector inside the above-mentioned cover.

It is further desirable to locate the above-mentioned heat generating block near the top opening of the above-mentioned frustum of the structure.

It is further desirable to hang a net-like container for holding a heat generator at the center of the upper end portion of a metallic frustum of a pyramid which is open in the bottom, one end side of the metallic pyramid cover being mounted on one top side of the above-mentioned frustum of the pyramid so that the cover can be opened or closed as desired, and include a heat insulating member, having a form corresponding to that of the above-mentioned net-like container, on the lower surface of the cover.

It is further desirable to provide vent holes in the above-mentioned frustum of the structure.

It is further desirable to provide a packing along the bottom edge of the above-mentioned frustum of the structure.

It is further desirable to provide handles on the external side surface of the above-mentioned frustum of the structure.

It is further desirable to use, as the above-mentioned heat generator, a moxa molding which is formed by adding a binder to carbonized moxa resulting from dry distillation of moxa in an inert gas and activated charcoal powder, kneading the mixture and molding the mixture into circular cylinders having a plurality of vent holes.

With the use of a moxa treatment device according to the above-described present invention, an affected part can be effectively heated and stimulated because the device, which is comprised of a hollow structure having the shape of a cone or pyramid which is open in the bottom and of a heat generating block which is located in the hollow structure, concentrates the thermal rays emanating from the heat generating block towards the bottom by reflecting them on the inner surface of the slanted side or sides of the hollow cone or pyramid.

The above-mentioned heat generating block is comprised of a heat generator and a porous heat generator supporting block. Hence air can be moved in and out through a large number of holes of the heat generator supporting block to facilitate the combustion of the heat generator loaded in the heat generator supporting block and, in turn, the radiation of thermal rays.

The above-mentioned hollow structure is comprised of a frustum of a cone or pyramid having an opening in the top and a cover which is installed on the top opening so that the cover can be opened or closed as desired, and moreover, as the above-mentioned heat-generating block is located inside the frustum of the cone or pyramid, a heat generator can be easily loaded in the heat generator supporting block located inside the frustum of the cone or pyramid by opening the cover.

Since a retainer which also serves as a heat reflector is provided inside the above-mentioned cover, leakage of thermal rays in the upward direction can be prevented.

Since the above-mentioned heat generating block is installed near the top opening of the above-mentioned frustum of the structure, the heat generator can be more easily loaded or unloaded, and the heat generating block can be stably retained by the retainer which also serves as a heat reflector, by closing the cover onto the top of the frustum of the structure.

The moxa treatment device can maintain the combustion of moxa over a long period of time, and the mean temperature during this period is as high as around 57° C. The moxa treatment device radiates thermal rays, that are necessary and sufficient for moxa treatment, towards the approximate center of the bottom opening in a concentrated manner. On the other hand, the temperature at the circumference of the bottom opening is as very low as around 30° C., and the bottom portion does not feel hot to the skin even if it is directly placed on the skin. Therefore, there is no danger of burning a patient, and the device assures high safety and easy handling.

Since vent holes are provided in the above-mentioned frustum of the structure, air can be fed to the heat generator in the heat generating block installed inside the frustum of the structure, to maintain the combustion of the heat generator.

When the bottom circumference of the above-mentioned frustum of the structure is provided with a packing, there is cushioning and the airtightness between the bottom of the frustum of structure placed on an affected part and the skin surface of the affected part. This, in turn, eliminates the feeling of physical discomfort to the affected part and improves the thermal efficiency of the thermal rays.

When handles are mounted on the exterior side of the above-mentioned frustum of the structure, the device can be held by a handle or handles and the frustum of the structure can be easily reciprocated along an affected part to radiate the thermal rays onto the affected part.

Since the carbonized moxa has been carbonized in advance, when it is ignited at the time of moxa treatment, it will not generate, in contrast with the conventional moxa, a large volume of smoke nor any offensive smell. Moreover, it has a strong caloric force. Hence it has, as a heat generator, a sufficient therapeutic effect. After combustion, ashes will not scatter, and the clearance work is quite easy.

BRIEF DESCRIPTION OF THE DRAWINGS

The invention will be better understood from the following detailed description taken in conjunction with the accompanying drawings, wherein.

DETAILED DESCRIPTION OF THE INVENTION

Figure 1:
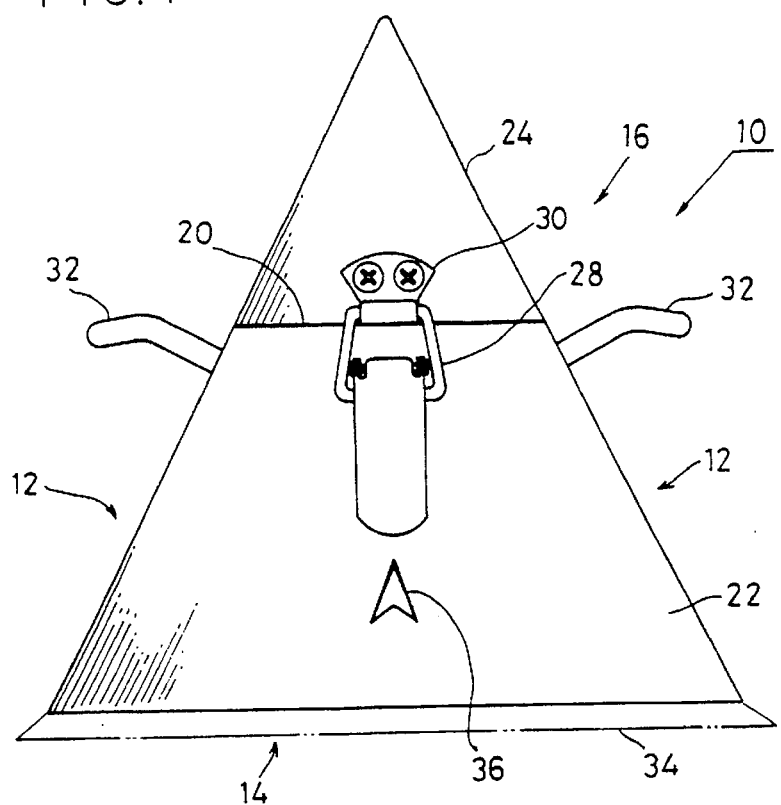
FIG. 1 is a front view of an embodiment of the moxa treatment device constructed according to the present invention.
Figure 5:
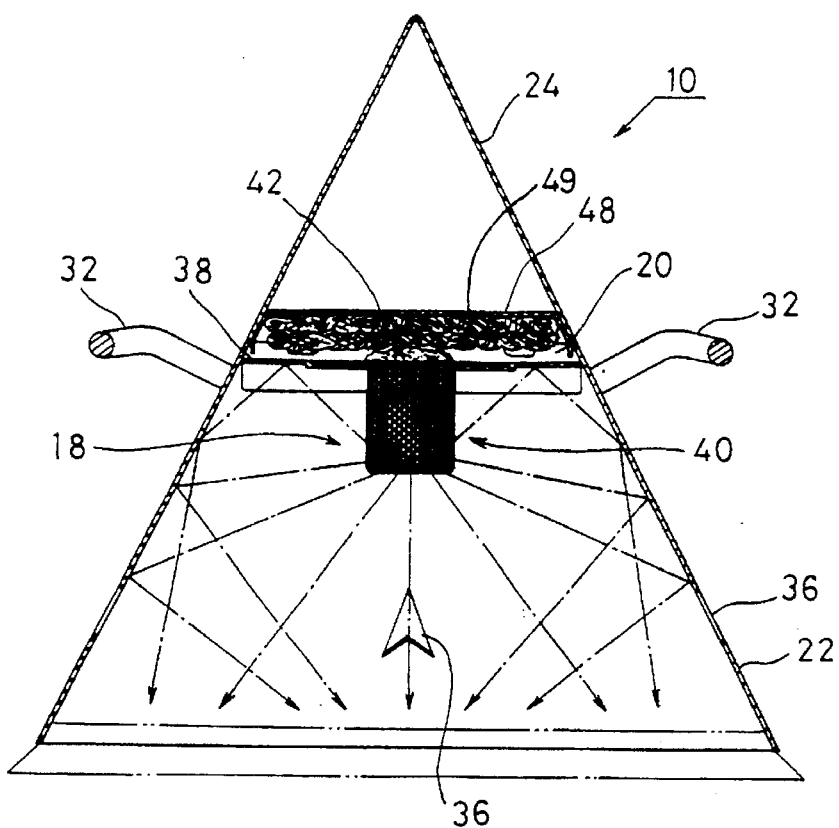
FIG. 5 is a sectional view taken on the line 5—5 of FIG. 3.

With reference to the attached drawings, a preferred embodiment of the present invention is illustrated in FIG. 1 and FIG. 5 which show a moxa treatment device 10 according to the present invention.

As clearly seen in the drawings, the moxa treatment device 10 includes a pyramid-like hollow structure in the shape of a regular quadrangular pyramid 16, formed by four slanted regular triangular faces or sides 12, and having an opening 14 in the bottom. A heat generating block 18 (FIGS. 4–6) is mounted inside the hollow regular quadrangular pyramid 16.

With this arrangement, the heat generated by the heat generating block 18 is directly projected towards the bottom opening 14 of the hollow regular quadrangular pyramid 16. Some of the heat is also reflected by the internal surfaces of the hollow regular quadrangular pyramid 16 and is projected towards the bottom opening 14. Thus the heat can be effectively concentrated onto an affected part of a person on whom the bottom of the hollow regular quadrangular pyramid 16 is placed. Moreover, since the thermal efficiency for an affected part is high, the volume of the heat generator 42 in the heat generating block 18 can be economized.

In the present specific example of the invention, the hollow regular quadrangular pyramid 16 is made of stainless steel. It is comprised of a frustum of regular quadrangular pyramid 22 having an opening 20 (FIGS. 1, 5 and 6) in the top, and of a regular quadrangular pyramid cover 24 which is mounted on the top opening 20 in such a way that it can be opened or closed as desired.

Figure 3:
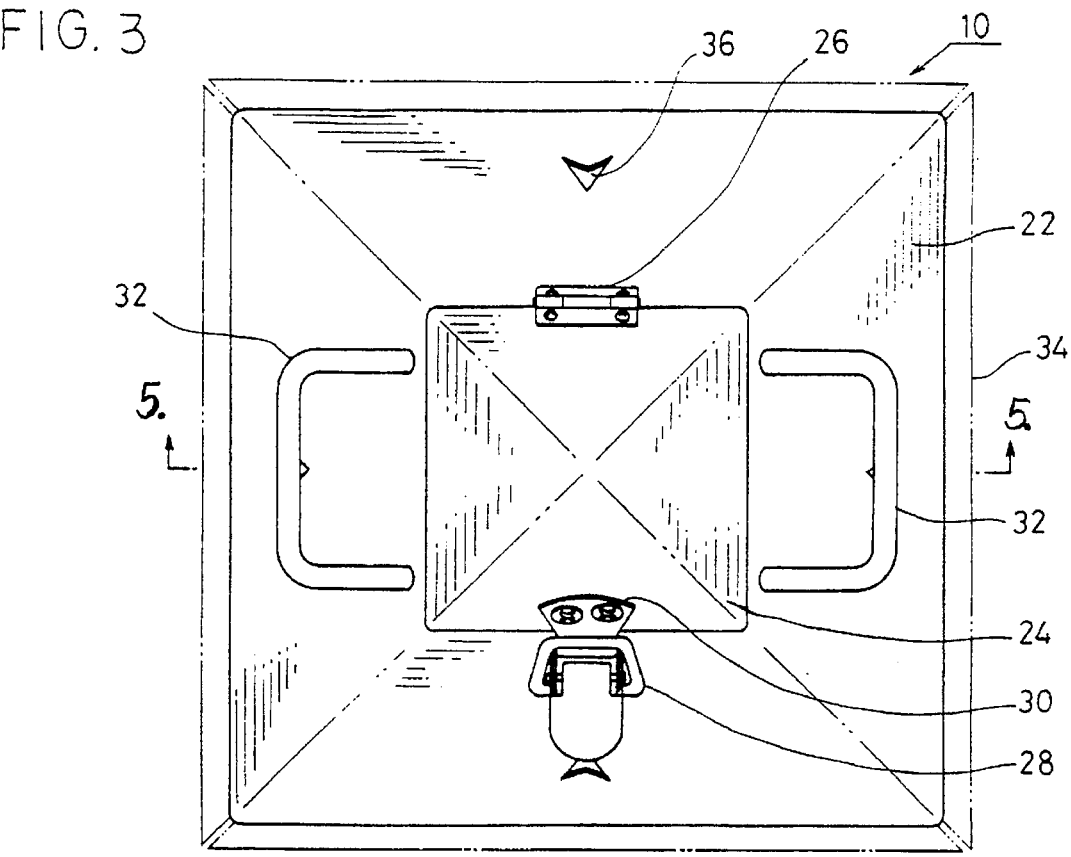
FIG. 3 is a top plan view of the moxa treatment device of FIG. 1.
Figure 4:
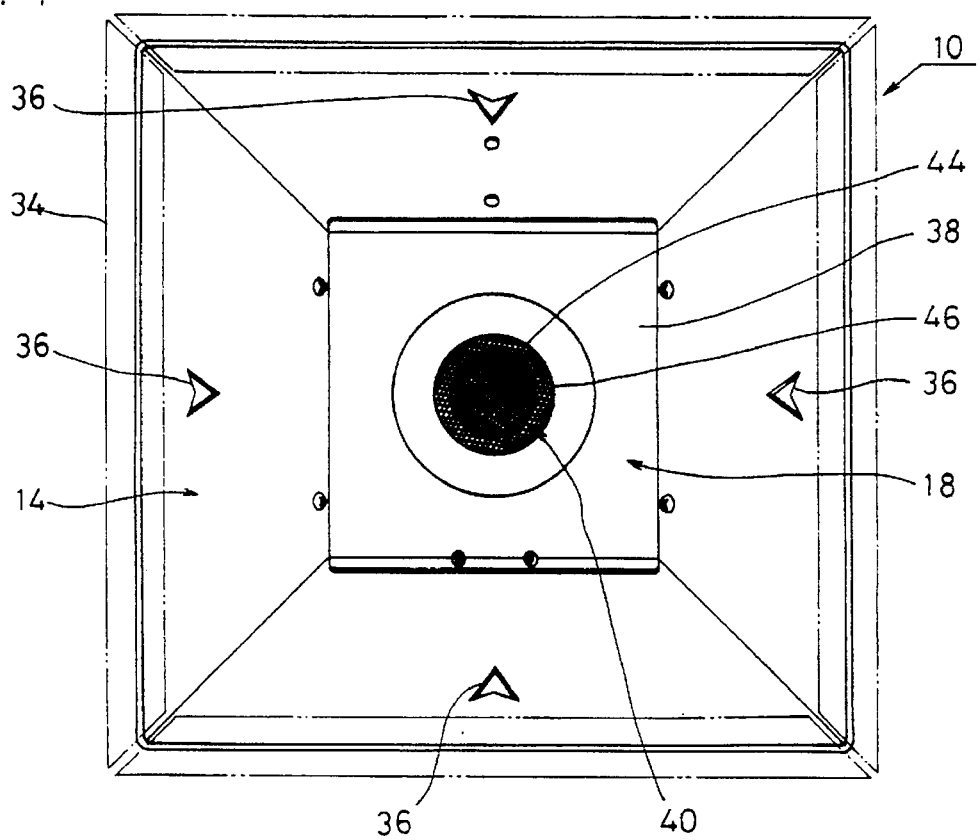
FIG. 4 is a bottom view of the moxa treatment device of FIG. 1.

In the present embodiment, the frustum of pyramid 22 and the cover 24 are formed, as shown in FIG. 3 and FIG. 4, into regular quadrangular pyramids. The structure may, however, have other forms which spread outwardly towards the bottom, such as cones, three-sided pyramids, etc. The material is not limited to stainless steel, because other materials such as other metals, ceramics, synthetic resins, etc. may be used provided that they have adequate corrosion resistance and heat resistance. When a material of poor reflectivity is used, it is desirable to use a reflecting plate or a reflecting sheet over the internal surfaces to concentrate the heat generated in the heat generating block 18 towards the center of the bottom opening 14.

Figure 2:
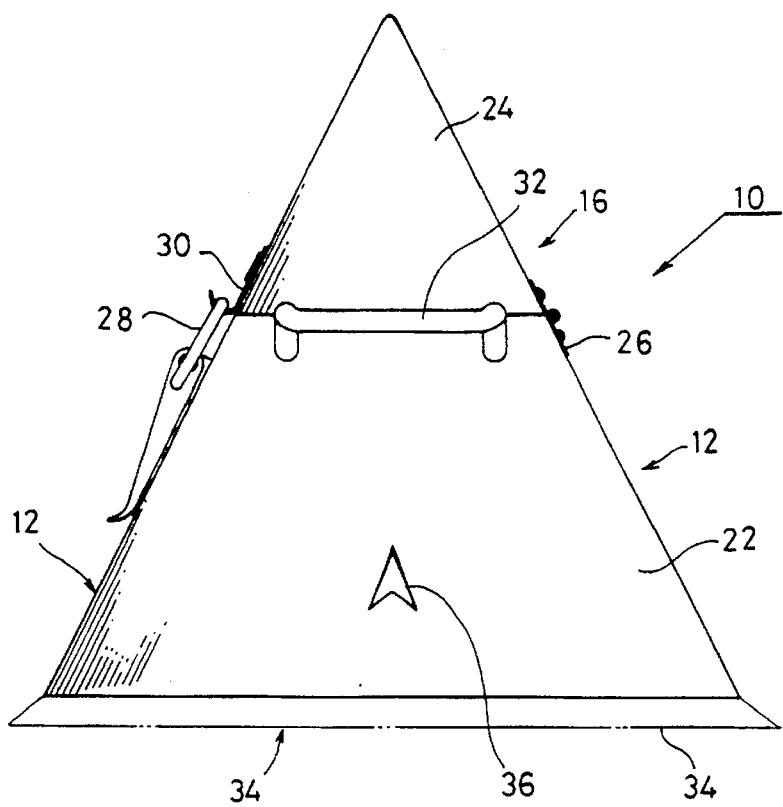
FIG. 2 is a right side view of the moxa treatment device of FIG. 1.
Figure 6:
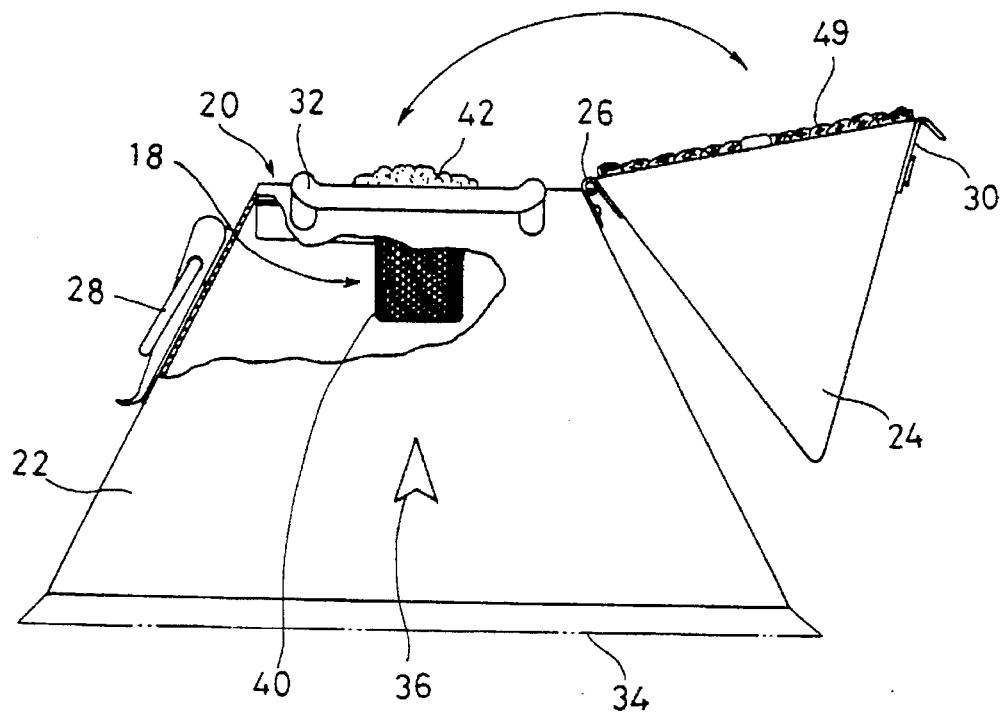
FIG. 6 partially cutaway right side view of the moxa treatment device having a cover which is open.

The cover 24 is mounted, as shown in FIGS. 2, 3 and 6, by a hinge 26 fixed to the external circumference of the top opening 20 of the frustum of the lower pyramid 22. A hook 30 (FIGS. 1 and 2) fixed to the cover 24 is disconnectably attached to a clasp 28 mounted on a slanted side 12 which is opposite to the hinge 26.

When the cover 24 is opened by disconnecting the hook 30 from the clasp 28, the heat generator 42 can be easily loaded into the heat generating block 18 inside the frustum of pyramid 22, and the heat generator 42 can be easily removed by disconnecting the hook 30 to open the cover 24. As shown in FIG. 1 and FIG. 3, two handles 32 are mounted on the frustum of pyramid 22 near the upper edge, in a direction which crosses an imaginary line connecting the hinge 26 and the clasp 28. Moreover, a packing 34 of an elastic material is provided along the circumference of the bottom opening 14 of the frustum of pyramid 22. As shown in FIG. 4, the respective slanted sides 12 of the frustum of pyramid 22 are provided with open vent holes 36. The number and the positions of the vent holes 36 are not limited to the two illustrated.

Hence the bottom opening 14 of the hollow regular quadrangular pyramid 16 of the moxa treatment device 10 can be stably placed on an affected part by holding the handles 32. The packing 34 improves the cushioning and the airtightness between the bottom opening 14 of the hollow regular quadrangular pyramid 16 and the skin surface of the affected part to prevent the heat projected from the heat generating block 18 towards the skin surface and the smoke of combustion from the heat generating block 18, from leaking between the pyramid and the skin surface.

Air is constantly fed through the vent holes 36 into the frustum of pyramid 22. Hence the combustion of the heat generator 42 in the heat generating block 18 can be maintained.

As shown in FIG. 4, FIG. 5 and FIG. 6, the heat generating block 18 is comprised of a porous heat generator supporting block which is open at the top and is made of stainless steel (hereinafter called a container) 40, and a heat generator 42 is loaded into this container 40. The material of the container 40 may be other metals, ceramics, synthetic resins, etc. provided that they have adequate corrosion resistance and heat resistance. Near the edge of the top opening 20 of the frustum of pyramid 22, a heat reflecting plate 38 having an open hole 44 in the center is fixed in such a way that the heat reflector 38 covers the top opening 20 around the container 40. The container 40, being in the form of an inverted derby hat and made of fine mesh of a heat-resistant metal, is inserted into the hole 44, and a flange 46 at the upper end of the container 40 is disconnectably held by the upper surface of the plate 38 having the hole 44. A heat generator 42 is loaded into the container 40 and ignited. Then the cover 24 is closed, and the hook 30 is attached to the clasp 28.

The container 40 is porous, and the heat generator 42 is sufficiently fed with air coming in through the vent holes 36. Thus the combustion of the material 42 is maintained. When the combustion of the heat generator 42 is terminated, the hook 30 may be released from the clasp 28 to open the cover 24. Then the container 40 may be removed from the hole 44 of the heat reflecting plate 38 and be easily reloaded with new heat generator material 42. The heat generator 42 may be ignited again and the cover 24 may be closed to continue the combustion.

The thermal rays generated from the heat generator 42 burning inside the container 40 are directly projected towards the bottom opening 14 of the frustum of pyramid 22 because the hollow regular quadrangular pyramid 16 is in a pyramid-like form. Some thermal rays from the heat generator 42 are also reflected by the internal surfaces of the sides which are slanted by 60 degrees relative to the horizontal plane of the frustum of pyramid 22 and projected towards the bottom opening 14. Hence, as shown in FIG. 5, the thermal rays are concentrated towards the approximate center of the bottom opening. This results in a high thermal efficiency. These thermal rays can be utilized to heat up and stimulate an affected part so as to assist self-healing.

Moreover, because the thermal efficiency of the thermal rays is high at the bottom opening 14, the charge of moxa to be burnt in the container 40 can be economized, and the combustion can be maintained over a long period of time.

In this example, moxa is used as a heat generator 42, but the material is not necessarily limited to moxa. For example, carbonized moxa (carbonized moxa which is molded into a pillar form), various herbs, and a heating wire which is available for connection to an electric power source may be loaded in the container 40, to project thermal rays.

Figure 7:
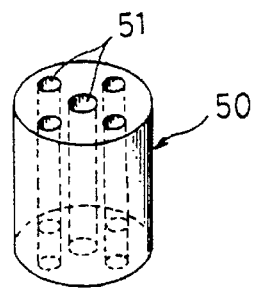
FIG. 7 is a perspective view showing an example of carbonized moxa well suited for use in the moxa treatment device of the embodiment of the present invention.

FIG. 7 shows an example of carbonized moxa. The carbonized moxa 50 is produced in the following manner: Moxa obtained from leaves of mugwort is subjected to dry distillation by holding it in an atmosphere of an inert gas, such as nitrogen gas, at temperatures of from 400° to 600° C. for 30 to 90 minutes. Then the moxa is cooled in the dry distilling atmosphere to obtain carbonized moxa. Powders of activated charcoal produced by carbonization of coconut husk, wood, etc. are then mixed with the carbonized moxa. Binders which do not produce much smoke nor offensive odor (such as carboxymethylcellulose and other water-soluble cellulose derivatives) are added to the mixture, and the resulting mixture is molded. The mixing ratio of the carbonized moxa and the activated charcoal powder is preferably one to one. The quantity of the binder is desirably from 5 to 20% of the mixture of the carbonized moxa and the activated charcoal. In this manner, the carbonized moxa is molded into pillars having a large number of vent holes 51. With regard to their dimensions, the diameter is about 20 mm and the length is about 25 mm. They are sized for easy loading into the container 40. The carbonized moxa 50 has been carbonized in advance. When it is ignited at the time of moxa treatment, it does not produce much smoke or offensive odor in contrast with the conventional moxa. It also has a high caloric force, and it gives a sufficient therapeutic effect when used as a heat generator 42. After combustion, the ashes do not scatter, and the cleaning work is very easy.

As shown in FIG. 5, a retainer which also serves as a heat reflector 48 is provided in the lower inside part of the cover 24. At the center of the retainer 48, a cover 49 made of asbestos (or fiberglass wool, for example) is replaceably installed as a heat insulator. The cover 49 has the function of retaining the heat generator 42 (moxa) in the container 40 and the function of an insulator, and prevents the cover from being excessively heated during use. When the top opening 20 of the frustum of pyramid 22 is closed by the cover 24, the upper opening of the container 40 will be closed by the retainer which also serves as a heat reflector 48. The heat generator 42 loaded into the container 40 will be stably held and the combustion will be continued. Moreover, the thermal rays projected upwards from the container 40 will be reflected downwards.

An example of the dimensions of a moxa treatment device 10 according to the present embodiment are as follows:

A stainless steel plate having a thickness of 0.5 mm is used as the material of the pyramid. The frustum of pyramid 22: The bottom opening =160×160 mm. The top opening =70×70 mm. The height =78 mm; The cover 24: The bottom opening =70×70 mm. The height—60 mm; The heat generating block: The diameter of the porous container 40=26 mm. The height =26 mm. It is made of SUS400 # mesh.

In use, moxa is loaded as a heat generator 42 into the heat generating block and ignited. The temperature at the approximate center of the bottom opening 14, with the bottom opening 14 of the frustum of pyramid 22 being closed (the condition of moxa treatment), is as shown in the lower row (fully closed state) of the following table:

| Time (min.) | 10 | 20 | 30 | 40 | 50 | 60 | 70 | 80 | Mean Temp. |
|---|---|---|---|---|---|---|---|---|---|
| Open | 60 | 73.1 | 77.3 | 76.7 | 71.3 | 64.4 | 58 | 57 | 67.23(°C.) |
| Closed | 49.3 | 57 | 60.3 | 61.5 | 61.7 | 59.8 | 56.5 | 52.4 | 57.31(°C.) |

Figure 9:
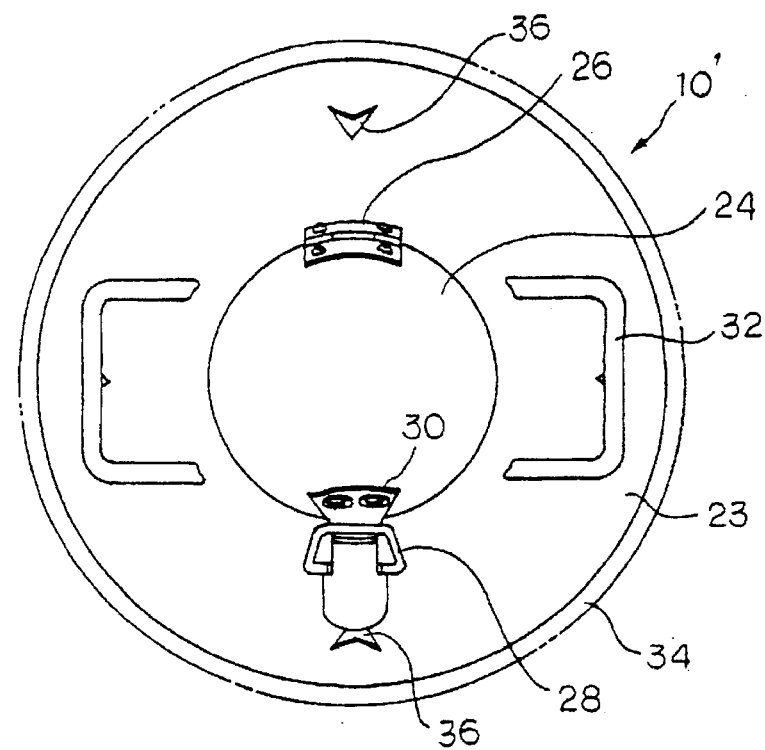
FIG. 9 a view similar to FIG. 3 but showing an alternative construction of the invention.
Figure 10:
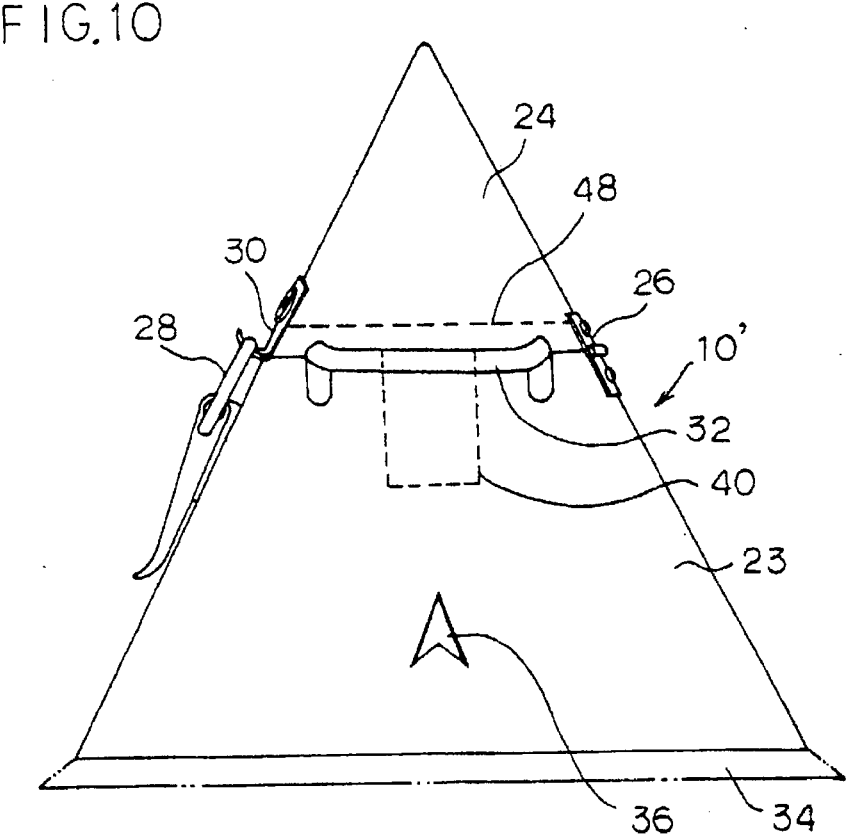
FIG. 10 is a view similar to FIG. 2 but showing the device of FIG. 9.

Ten minutes after the ignition, the temperature reached 49.3° C., and 40 minutes after, it reached 61.7° C. The combustion was maintained for 80 minutes. During this period, the mean temperature was 57.31° C. The upper row indicates the temperature at the approximate center of the bottom opening when the bottom opening 14 was kept open. The temperature at the circumference of the bottom opening 14 Of the frustum of pyramid 22 was as very low as around 30° C. Hence the bottom portion will not feel hot even if the skin directly contacts the bottom portion. Thus the device 10 may be used without the above-mentioned packing 34. As explained so far, temperatures sufficient for giving moxa treatment effects can be maintained at the central area in a concentrated manner over a long period because the above-mentioned hollow regular quadrangular pyramid 16 is selected for the form of cone or pyramid. Moreover, the circumference of the bottom opening of the frustum of pyramid 22 does not get hot. Hence it is best suited to the moxa treatment device. The desired shape, however, is not limited to the above-mentioned one. The structure may be formed into a circular cone as shown in FIGS. 9 and 10.

In contrast, one example of the conventional moxa treatment devices is a cylindrical holder. It is made of wood. The outer diameter =50 mm approx. The inner diameter =40 mm approx. The height =60 mm approx. A holding block for loading moxa therein is provided at the top end of this cylindrical holder. The moxa is formed into a cigarette form with the diameter =10 mm approx. and the length =25 mm approx. When the lower end of the cigarette-shaped moxa is ignited and the moxa is inserted into the middle height position inside the cylindrical holder, the temperature at the bottom opening of the cylindrical holder is about 40° C. The combustion of a moxa in the cigarette form is completed within 15 or 20 minutes approximately.

Thus the moxa treatment device 10 according to the present invention, in contrast with moxa treatment with the conventional cylindrical holder, can project thermal rays of higher temperatures, consumes less moxa, and can project thermal rays over a longer period of time.

Figure 8:
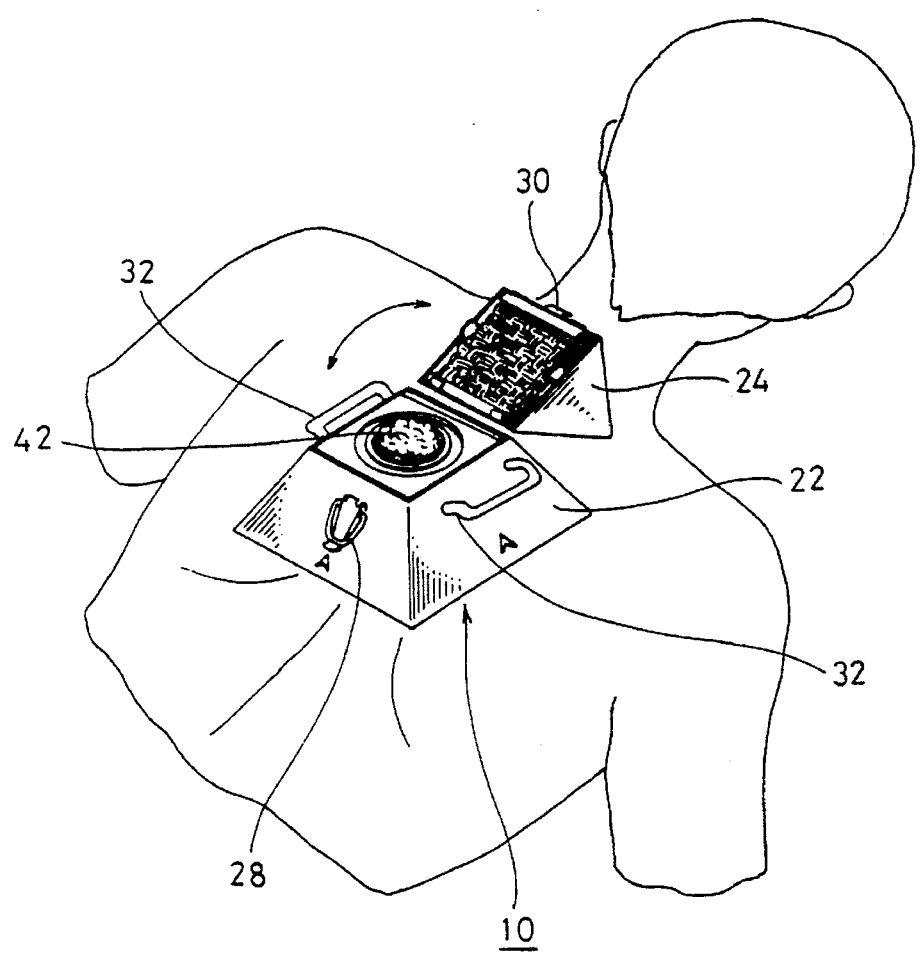
FIG. 8 is a perspective view illustrating the moxa treatment device placed on the back of a person, with the cover open and moxa loaded in the heat generating block inside the device.

The use of the moxa treatment device 10 according to the present invention is described as follows. When the moxa treatment device 10 is used to relieve the pain of an affected part, such as a person's back as shown in FIG. 8, the hook 30 of the cover 24 is disconnected from the clasp 28 on the side of the frustum of pyramid 22, and the cover 24 is rotated with the hinge 26 as the center of rotation to the open position.

The porous container 40 of the heat generating block 18, which is mounted near the circumference of the top opening 20 of the frustum of pyramid 22, is taken out of the hole 44 in the heat reflecting panel 38. A heat generator 42 is loaded into the container 40 and the heat generator 42 is ignited. Then the container 40 is placed in the hole 44 of the heat reflecting plate 38.

Then the cover 24 is rotated towards the top opening 20 of the frustum of pyramid 22 to close the opening 20. Moreover, the hook 30 is attached to the clasp 28 of the frustum of pyramid 22.

The frustum of pyramid 22 can be stabily held on the surface of an affected part. The thermal rays coming from the heat generator 42, which is burning in the frustum of the pyramid 22, are directly projected towards the bottom opening 14 of the frustum of pyramid 22. Some of the thermal rays are reflected by the internal surfaces of the frustum of pyramid 22 to be projected towards the bottom opening 14. Thus the thermal rays effectively heat up an affected part. There is no need of adjusting the heat generator 42 burning in the container 40, and the combustion can be maintained over a long period of time.

The opening 14 in the bottom of the frustum of pyramid 22 may be directly placed on the skin surface of an affected part. If the thermal rays are too excessive, a piece of sheet material may be placed over the top of the affected part and the moxa treatment may be given through the sheet.

The frustum of pyramid 22 can be freely moved by holding the handles 32 thereof along an affected part to concentrate the thermal rays towards the affected part. The smoke of combustion of the heat generator 42 may be kept inside the frustum of pyramid 22 to expose the affected part to the smoke. In this way, the surface of the affected part can be sterilized.

FIGS. 9 and 10 illustrate a moxa treatment device 10' which functions similarly to the device 10 but has the shape of a hollow cone instead of a hollow pyramid. While the outer shape is different, the substantive operating parts, such as a container 40 and a retainer, etc., are common to the two devices 10 and 10'. Only the hinge 26' differs slightly from the hinge 26 because the hinge 26' is curved slightly to fit the curved surface of the cone. The hinge pin of the hinge 26' may be sufficiently loose fitting to enable the hinge to function even though the pin is curved slightly.

As will be clear from the explanation above, the invention has the following advantages or effects:

With the use of a moxa treatment device according to the present invention, an affected part can be effectively heated and stimulated because the thermal rays generated from the heat generating block are reflected by the inner surface of the tilted side or sides of the hollow cone or pyramid towards the open bottom. Moreover, since the thermal efficiency of the thermal rays towards the bottom opening is high, the volume of the heat generator in the heat generating block can be economized, and the combustion can be maintained over a long period of time. Hence the pain of the affected part can be fully relieved, and the moxa treatment device can be held stabily on the surface of the affected part. There is no need for adjusting the ignition block and the device does not require much trouble during treatment.

Because the air can be moved in and out through a large number of holes in the container, the heat generator loaded in the container can be easily burnt to project thermal rays.

A heat generator can be easily loaded in or unloaded from the heat generating block located in the frustum of the cone or pyramid-shaped structure, by opening and closing the cover.

The leakage of thermal rays in the upward direction can be prevented, and the increase in thermal rays being projected towards an affected part improves the effectiveness of the moxa treatment.

Because the heat generator can be more easily loaded or unloaded, it is easy to give moxa treatment over a long period of time by supplementing the heat generator. Moreover, as the heat generating block can be stabily retained by the retainer that also serves as a heat reflector by closing the cover onto the top of the frustum of cone or pyramid, the position of the heat generating block will not shift inadvertently when the moxa treatment device is moved. Thus no adjustment is needed.

Since a sufficient temperature for moxa treatment effects can be maintained at the bottom center in an concentrated manner over a long period of time, moxa treatment can be given continuously over a long time. Moreover, as the circumference of the bottom opening does not get very hot, the device is easy to handle.

Air can be constantly fed to the heat generator in the heat generating block installed inside the frustum of cone or pyramid to easily maintain the combustion of the heat generator.

As the cushioning between the bottom of the structure being placed on an affected part and the skin surface of the affected part is improved, the affected part will not feel any physical discomfort against the structure. Moreover, as the airtightness is improved, the thermal efficiency of thermal rays is improved, resulting in greater effectiveness of the moxa treatment.

Because the frustum of cone or pyramid-shaped structure can be easily reciprocated along an affected part by holding the handles to radiate the thermal rays onto the affected part, the effectiveness of the moxa treatment is improved.

When the heat generator is ignited, it will not generate, in contrast with the conventional moxa, a large volume of smoke or any offensive smell. Moreover, it has a strong caloric force. Hence it has, as a heat generator, a sufficient therapeutic effect. After combustion, ashes will not scatter, and the clearance work is quite easy.

What is claimed is:

1. A moxa treatment device comprising a hollow structure having the shape of a hollow cone or pyramid, said structure having an open bottom, and a heat generating block installed inside said hollow structure, said heat generating block comprising a heat generator and a porous supporting block for said heat generator, said hollow structure comprising a frustum of a cone or pyramid having a top opening and a cover which is mounted on said top opening in such a way that said cover can be freely opened and closed as desired, and said supporting block being provided inside the frustum of said hollow structure.

2. A moxa treatment device as set forth in claim 1, and further comprising a retainer for said supporting block, said retainer being provided inside said cover and also serving as a heat reflector.

3. A moxa treatment device as set forth in claim 1 or claim 2, wherein said heat generating block is mounted near an edge of said top opening of said frustum of said structure.

4. A moxa treatment device comprising a netlike container for holding a heat generator, a metallic cone or pyramid which is open in the bottom and has a frustum, said cone or pyramid supporting said container at an upper end portion thereof, a metallic cover having one side mounted on the top side of said frustum of said cone or pyramid such that said cover may be opened or closed as desired, and a heat insulating member having a shape corresponding to that of said net-like container, installed on the lower surface of the cover.

5. A moxa treatment device as set forth in claim 1 or claim 4, wherein said frustum of said cone or pyramid is provided with vent holes.

6. A moxa treatment device as set forth in claim 1 or claim 4, wherein a lower circumference of said cone or pyramid is provided with a packing.

7. A moxa treatment device as set forth in claim 1 or claim 4, wherein said cone or pyramid includes an external side surface, and handles are provided on said external side surface of said cone or pyramid.

8. A moxa treatment device of claim 3 or claim 4 wherein said heat generator comprises a moxa molding which is formed by adding a binder to carbonized moxa resulting from dry distillation of moxa in an inert gas and activated charcoal powder, kneading the mixture and molding the mixture into circular cylinders having a plurality of vent holes.

* * * * *

UNITED STATES PATENT AND TRADEMARK OFFICE
CERTIFICATE OF CORRECTION

PATENT NO. : 5,632,768

DATED      : May 27, 1997

INVENTOR   : Osamu SHIMADA

It is certified that error appears in the above-identified patent and that said Letters Patent is hereby corrected as shown below:

Column 10, line 35, "claim 3" should be --claim 1--.

Signed and Sealed this

Twenty-third Day of March, 1999

Attest:

Q. TODD DICKINSON

*Attesting Officer*     *Acting Commissioner of Patents and Trademarks*